United States Patent [19]

Langerholc et al.

[11] Patent Number: 4,555,179
[45] Date of Patent: Nov. 26, 1985

[54] DETECTION AND IMAGING OF OBJECTS IN SCATTERING MEDIA BY LIGHT IRRADIATION

[76] Inventors: John Langerholc, Paul-Klee-Str. 8, 8000 Munich 71; Thorsteinn Halldórsson, Lerchenauerstrasse 2, 8 Munich 40, both of Fed. Rep. of Germany

[21] Appl. No.: 439,867

[22] Filed: Nov. 8, 1982

[51] Int. Cl.[4] ............................................. G01N 21/00
[52] U.S. Cl. ..................................... 356/342; 356/237
[58] Field of Search ...................... 356/52, 53, 66, 342, 356/237, 239, 446; 250/563, 572; 128/633, 665

[56] References Cited

U.S. PATENT DOCUMENTS 3,976,384 8/1976 Matthews et al. ............... 356/239 X
4,314,763 2/1982 Steigmeier et al. .............. 356/342 X

FOREIGN PATENT DOCUMENTS 2751365 12/1979 Fed. Rep. of Germany .
2933066 2/1981 Fed. Rep. of Germany .

OTHER PUBLICATIONS

In Applied Optics 18, 2286 ff, (1979).

Primary Examiner—Davis L. Willis
Assistant Examiner—Matthew W. Koren
Attorney, Agent, or Firm—W. G. Fasse; D. H. Kane, Jr.

[57] ABSTRACT

A method and system are described for the detection and imaging of objects and structures in scattering media using light radiation. The medium is scanned with a strongly collimated light beam (2). The light power ($P_b$) scattered backward from the medium is detected by a receiver (17) and plotted along the scanning path. Objects (4) buried in the medium (9) are detected by the differential variation of the received light power. Information as to the size, location and depth of the objects can be obtained. The illumination by strongly collimated laser light at one or several wavelengths is preferred.

15 Claims, 11 Drawing Figures

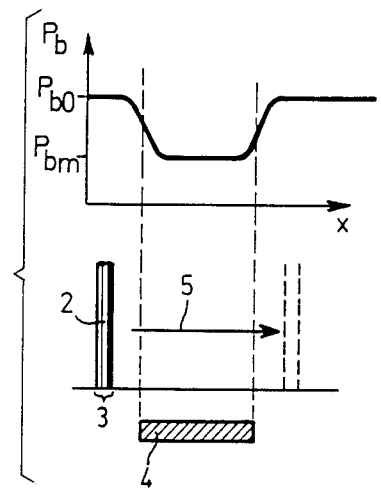
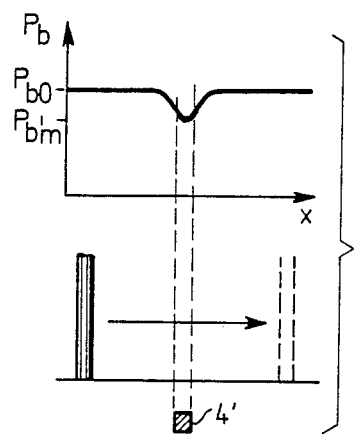
FIG. 4a FIG. 4b
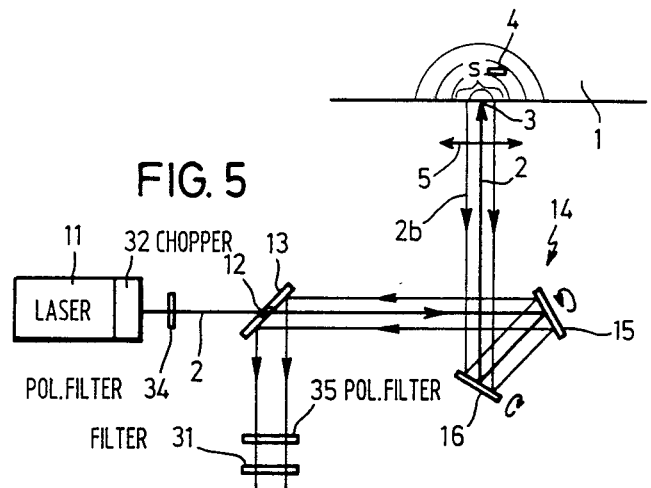
FIG. 5
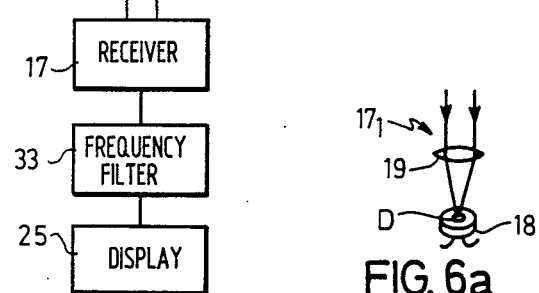
FIG. 6a
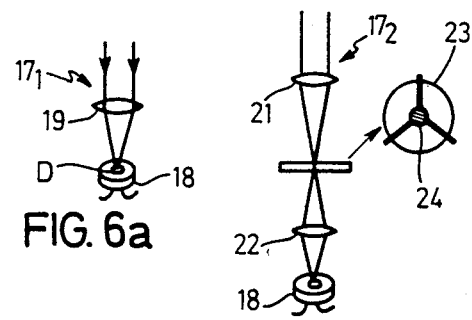
FIG. 6b

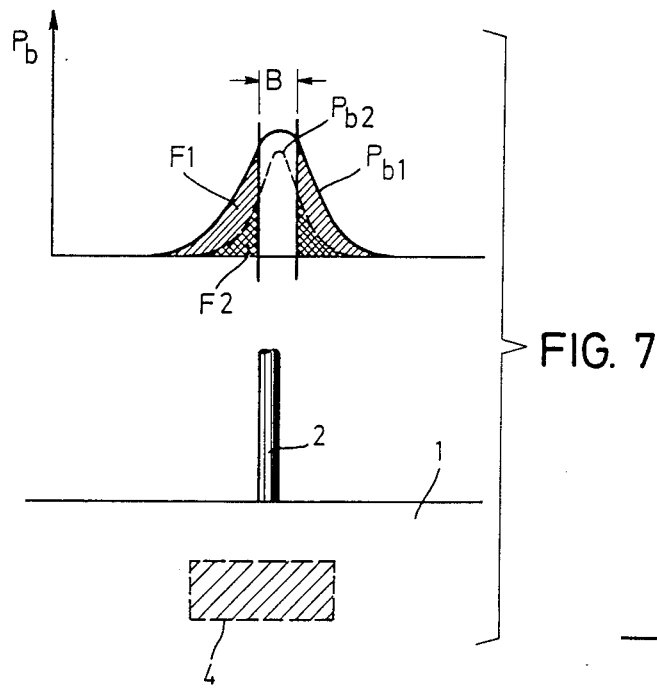
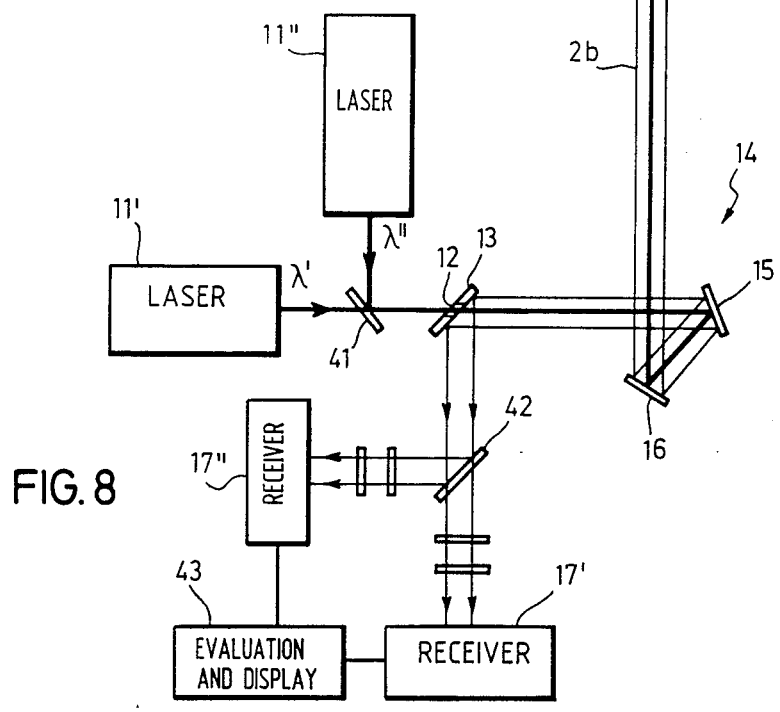
FIG. 7
FIG. 8

DETECTION AND IMAGING OF OBJECTS IN SCATTERING MEDIA BY LIGHT IRRADIATION

BACKGROUND OF THE INVENTION

This invention relates to a system for detecting and imaging objects and structures surrounded by scattering media using light irradiation.

The detection of objects and structures surrounded by a weakly absorbent scattering medium poses a difficult problem in diverse technical fields. For example, traffic technology seeks to achieve sighting of large objects in fog. In medicine, the observation of morphological and anatomical structures in the organs and periphery of the human body is frequently useful. Materials technology has long sought effective methods for detection of flaws and inhomogenities in translucent substances which are not transparent.

For the imaging of objects or structures surrounded by scattering media, transillumination procedures (diaphanoscopy) are customarily employed, in which the object or structure is recognized on the basis of the shadow edges it produces in the scattered light emanating from the opposite side if the medium. Such transillumination processes are applied in medicine, for instance, to determine the course of blood vessels in tissue layers.

Such transillumination procedures are also used to determine the absorptivity of a medium containing scattering or absorbing particles. By measuring the absorption, the concentration of the particles in the medium may be determined. For the state of the art of absorption measurements, see DE-AS No. 2,751,365 and DE-OS No. 2,933,066.

Whether for the detection of objects or the determination of the particle concentration in a scattering medium, the use of a transillumination procedure requires that both sides of the medium be accessible. This is often not the case, however. In the example from the field of medicine in which blood vessels are to be detected in tissue, the tissue layers are often too thick optically to allow the light to pass through. Transillumination procedures are thus inapplicable to such cases.

It is here that the invention can be applied to solve the problem of providing a procedure and apparatus for the detection and imaging of objects and structures surrounded by a scattering medium by means of illumination of and detection from one and the same side of the medium.

The invention is based on recognition of the following facts: if a collimated light beam falls on a scattering medium, at every point along its path inward a portion of the light is absorbed and a portion is scattered. Depending on the size, constitution and density of the scattering centers and the polarization state of the incident light, the scattering can display a variety of predominant behaviors including forward, backward or isotropic characteristics. In the cases discussed here of extremely dense scattering media, which render the buried objects invisible to conventional examination, the scattering can be adequately treated by a model in which the elementary scattering process is isotropic and independent of polarization so that the residual component of the incoming light retains its original polarization. According to this model, the incoming radiation is distributed by multiple scattering inside the medium as follows: the light beam will be considerably broadened inside the medium by virtue of the scattering process. The magnitude of this effect increases with the effective depth of the medium; the residual component of the incoming beam is strongly extinguished due to absorption and scattering of the light in all directions away from the orientation of the incoming beam. Beyond a depth corresponding to the extinction coefficient of the medium for the wavelength of the incoming light beam, the light transport is basically a diffusion process in the radial direction. Assuming that the absorptivity of the medium is low, a large percentage of the incoming light will be returned by virtue of multiple scattering from various depths back to the surface of the medium and be reemitted. This gives rise to a "scattering zone" centered at the position of incidence of the incoming beam and, in the case of visible light, appears as a brightly glowing spot that can have a diameter much greater than that of the incoming beam. In *Applied Optics* 18, 2286 ff (1979), the distribution of the total power $P_o$ incident on a slab of scattering material into the various modes is plotted as a function of the slab depth. The modes of distribution of the light energy are: $P_r$ the residual beam power reaching the rear wall; $P_f$ the power scattered forward out of the slab; $P_b$ the power scattered backwards in the direction of the beam's source; $P_a$ the power absorbed by the medium. The dependence of the backscattered power on the depth of a sample of a scattering medium can be used to infer the existence of a strongly absorbing region (object or structure) beneath the surface, which has the effect of a local reduction of the thickness of the scattering medium. A global evaluation of the fluctuation of the local depth as a function of the scanning position can, therefore, be utilized for the detection and imaging of objects "buried" in the scattering medium which would not be visible on diffuse illumination of the surface of the medium.

OBJECTS OF THE INVENTION

In view of the above it is the aim of the invention to achieve the following objects singly or in combination:

to provide a system for detecting and imaging objects surrounded by scattering medium, where only one side of the scattering medium is accessible and where conventional transillumination procedures are therefore inapplicable;

to provide methods for detecting and imaging objects immersed in material too thick optically for light to pass through as, for example, in the field of medicine where blood vessels are to be detected in thick tissue layers;

to provide methods for imaging objects and structures surrounded by inhomogeneous and anisotropic media and for imaging within materials themselves inhomogenities and anisotropies;

to provide new methods and apparatus for examination of materials, for medical investigations such as detection of foreign bodies, and generally for locating objects hidden by weather conditions or in a body of water or the like; and to provide a new method for illumination and detection of objects immersed in the scattering medium in which illumination and detection may occur on the same side of the medium around the locus of the incident illuminating beam of light.

SUMMARY OF THE INVENTION

The invention thus makes use of the recognition that the mean diameter of the intensity (irradiance) distribution of the scattered light in the scattering zone as well as the total power contained in the backscattered radiation in any scattering direction is strongly dependent on the depth (thickness) of the scattering medium. These parameters are a sensitive indication of the thickness of the layer of the medium covering an absorbent object, i.e., the depth at which the object is located. An image of objects beneath the surface may then be reconstructed from the fluctuation and geometrical distribution of the light backscattered from the interior of the medium back through the obverse surface of the medium. For this purpose, the medium is scanned along a path by a collimated light beam which penetrates into the medium. The amount of light reemerging from the medium in the region of the scattering zone centered about the position of incidence of the light beam is measured and plotted along the scanning path. Then the plot locations at which the intensity or power of the returned light differs from the mean values on both sides along the scanning path can be uniquely attributed to the presence of an object. If, for example, a strongly absorbent body lies along the path of the incident light beam in the medium, then the light power backscattered while scanning the region of the medium covering the body will be strongly attenuated and thus be recognizable differentially. If the body is strongly reflecting, on the other hand, the total backscattered power will be much greater than the undisturbed backscattering and thus be differentially recognizable.

The essential point is that the surface of the medium be scanned pointwise with a strongly collimated beam, for instance a laser beam. This has the advantage that the individual scattering zones, whether produced by undisturbed scattering or influenced by an object, appear separately in temporal succession and can thus be individually detected and evaluated one after the other. Using diffuse, or areal illumination of a strongly scattering medium, it generally proves hopeless to attempt detection even of objects lying close beneath the surface of the medium. This is because the individual rays of the light source falling on the medium produce scattering zones at every point, and the collective superposition of these scattering zones blurs the contrast produced by the differences in the total backscattered radiation.

A device for the detection and imaging of buried objects should preferably employ a laser beam guided across the surface of the medium in a scanning raster. This can be accomplished for example, by means of a scanning mirror arrangement comprising deflection mirrors rotating about different axes. The backscattered light can be guided back over the same scanning mirror arrangement and a duplexing mirror to the receiver which measures the quantity of backscattered light. This latter is then plotted as a function of the scanning path and evaluated according to the above mentioned criteria.

In the previous exposition of the idea of the invention, it was assumed that the scattering media under consideration possessed a well defined smooth surface and that the scattering centers were homogeneously distributed within the medium. This is, however, not always the case as demonstrated by the surface and density fluctuations of mobile media such as fog. Large inhomogenities in such media and surface irregularities influence the optical backscattering in a manner similar to absorbing or reflecting objects or structures hidden in the medium and would thus critically hamper the imaging of the objects and structures aimed at in the procedure as described above.

The further idea of the invention, on which this improvement of the procedure is based, derives from the recognition that many scattering media of inhomogeneous density display similar absorption and scattering behavior over broad spectral regions of optical radiation. Such is the case for fog in the region from 400 nm to 2000 nm, for instance. That the scattering cross-section of these media is essentially constant over broad regions is basically due to the fact that the scattering centers are much larger than the wavelengths of light in the visible and infrared region and that in addition the index of refraction is approximately constant over this spectral range.

With respect to the plotting process, this means that within the above mentioned spectral region, the scattering produces both qualitatively and quantitatively the same distribution in the medium irrespective of the wavelength of the source of the light (the laser) as long as no objects are buried in the medium which absorb in a spectrally selective manner. In particular, the scattering distribution in a medium of fluctuating density is independent of the wavelength. The surface absorption characteristics of most solid objects, aside from completely white or black bodies, remain by no means constant in the visible or near infrared region, rather they display strong fluctuations according to the color toning of the object.

In order to obtain unambiguous correspondence between objects or structures the measured signals in spite of any inhomogenity in the medium the latter is scanned according to the invention by two light beams of differing wavelength entering the medium at the same position. The backscattered light radiation is afterwards separated and the light of each wavelength is guided to a separate detector. The signals measured by the detector are corrected to compensate for fluctuation of the output signal of the light sources (lasers) and calibrated with respect to differences in the mean output power of the two lasers and sensitivity of the detectors. Finally, the difference of the signals at the two wavelengths is formed. Because of the identical scanning geometry and the equality of scattering behavior of the medium at the two wavelengths, the difference signal is independent of whether or not the medium has a well defined surface. In the case where the medium is bounded by a surface, the difference signal is independent of the surface contours as well as inhomogenities such as density fluctuations and holes inside the medium.

Under ideal conditions, thus, the difference signal is zero. Slight differences resulting from possible differences in absorption and scattering in the medium at the two wavelengths or in the measurement geometry (for instance, different transmission in the transmitter or receiver channel, different beam divergence, different field of view, different detector sensitivity, etc.) which cannot be eliminated by the above mentioned calibration measures can be subsequently recognized as an offset signal and eliminated by means of standard electronic procedures.

In the two-wavelength procedure for imaging, the difference signal can be used without further processing for the subsequent evaluation stages, which are then identical to the imaging of hidden objects or structures described above using light of a single wavelength.

There is in principle nothing to preclude extension of the two-wavelength technique to a multispectral imaging process using more than two different wavelengths and a corresponding number of receiving channels;

such techniques would be applicable above all for various diagnostic purposes in the field of medicine. The individual spectral components can be evaluated on line by computer in various relationships prior to display, depending on the specific absorption characteristics of the objects to be detected, for instance by known image processing techniques of remote detection.

BRIEF FIGURE DESCRIPTION

In order that the invention may be clearly understood, it will now be described, by way of example, with reference to the accompanying drawings, wherein:

FIG. 4a is a schematic representation of a single scan of a scattering medium in which an object is buried and the graph of the plotted light intensity along the scanning path for the case in which the buried object has a diameter much greater than the collimated light beam;

FIG. 4b is a schematic representation of a single scan of a scattering medium in which an object is buried and the graph of plotted light intensity along the scanning path for the case in which the buried object has a diameter smaller than or on the order of that of the light beam;

FIG. 5 is a schematic representation and block diagram of a device for imaging an object buried in a scattering medium;

FIG. 6a is a schematically represented diagram of a first embodiment of a receiver for the device represented in FIG. 5;

FIG. 6b is a diagrammatic view of a second embodiment of a receiver for the device represented in FIG. 5;

FIG. 7 is a diagram and accompanying graph representing differential variations of the intensity profile of the scattering zone around the position of incidence of the light beam for undisturbed scattering and for scattering disturbed by the presence of an absorbent buried object; and FIG. 8 is a schematic representation and block diagram of a device for the imaging of objects buried in a scattering medium by means of two light beams of different wavelength.

DETAILED DESCRIPTION OF PREFERRED EXAMPLE EMBODIMENTS AND OF THE BEST MODE OF THE INVENTION

Figure 1:
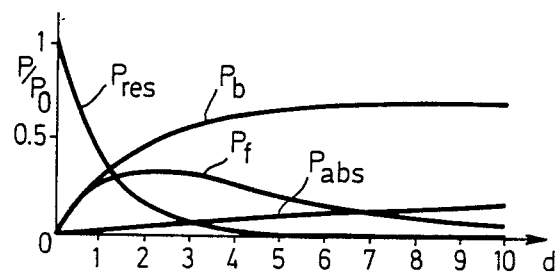
FIG. 1 is a graph displaying the relationship of the residual power, the absorbed power, and the forward and backward scattered power in biological tissue considered as a scattering medium as a function of the thickness of the tissue sample on irradiation of the tissue with laser light.

FIG. 1 shows how the input power $P_o$ of the incoming light beam distributes itself as a function of the thickness d of the tissue sample among residual power $P_{res}$, i.e., the amount of the original undeflected beam leaving through the rear wall, the power absorbed by the tissue $P_{abs}$, the forward scattered power $P_f$ and the backward scattered power $P_b$. It is seen from this plot that the backscattered power $P_b$ provides a sensitive indication of the thickness or depth d of the medium. The entire backscattered light is concentrated in the region of the so-called scattering zone about the position of incidence of the collimated laser beam.

Figure 2A:
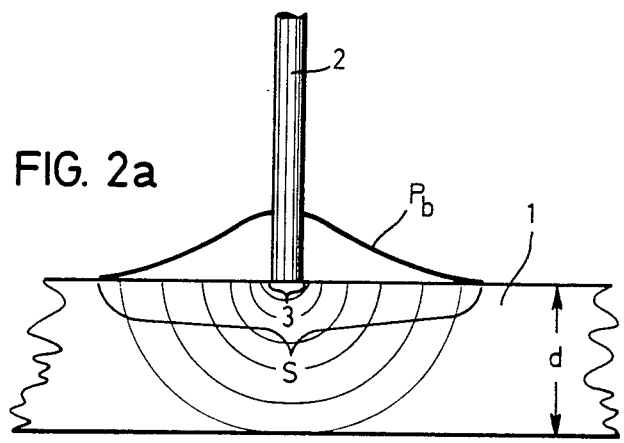
FIGS. 2a and 2b are diagrammatic side views showing the intensity distribution of the backscattered light for different thicknesses of the scattering medium.

FIG. 2 shows the intensity distribution of the backscattered light power in the scattering zone S for various thicknesses d of the irradiated medium. In FIG. 2a, a relatively thick medium sample 1 is illuminated by a collimated laser beam 2 normal to the surface of the medium and enters the medium in region 3. The scattering zone S appears as a relatively large disc at the surface of the medium in which the intensity of the backscattered light radiation $P_b$ is distributed according to a bell shaped curve over the region of the scattering zone. The scattering zone S has a diameter of $2\frac{1}{2}$ times the thickness d of the medium in this case.

Figure 2B:
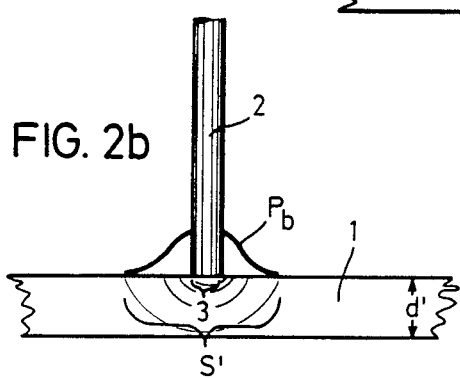

In FIG. 2b, the same medium 1 with smaller thickness d' corresponding to about $\frac{1}{2}$ that of FIG. 2a, however, is irradiated by the laser beam 2 with the same power $P_o$. The diameter of the scattering zone S' produced thereby is again roughly $2\frac{1}{2}$ times as great as the thickness d' of the medium; the diameter of the scattering zone S' is thus smaller than that of the scattering zone S in the ratio of the thicknesses d/d'. In addition, the maximal value of the backscattered light power $P_b$ corresponding to the diagram in FIG. 1 is smaller than the maximal value in FIG. 2a.

Figure 3:
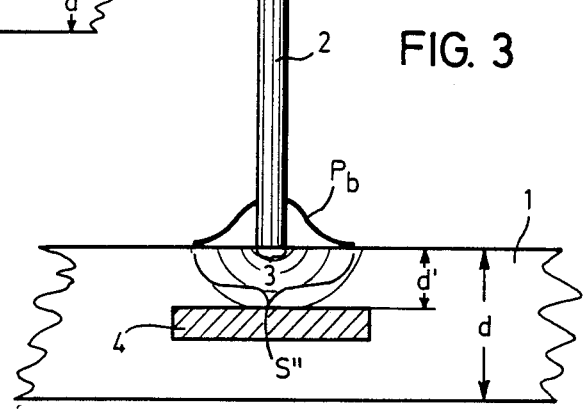
FIG. 3 is a diagrammatic side view showing the intensity distribution of the backscattered light in the event of an absorbing object buried in the medium.

In FIG. 3, medium 1 with a thickness d is irradiated as in FIG. 2a by a laser beam 2. A strongly absorbent object 4 having a surface area much larger than the laser beam entering region 3, is located at a depth d' corresponding to FIG. 2b in the path of the laser beam 2. The intensity distribution of the backscattered light power $P_b$ within the scattering zone S" corresponds roughly to the distribution shown in FIG. 2b. Here the diameter of the scattering zone S" and the maximal value of the backscattered light power $P_b$ depend on the absorptive behavior of the object 4. Therefore, if one knows the absorption properties of the object 4 and its extent, the depth at which the object lies beneath the surface of the medium can be determined as well from the shape of the intensity profile of the light power within the scattering zone.

In order to detect such objects 4 surrounded by a scattering medium 1, the medium is scanned with the laser beam 2 in the direction of the arrow 5. During the scanning the instantaneous value of the backscattered power $P_b$ is measured. FIG. 4a shows the situation of an object the surface extent of which is much larger than the entering region 3 of the incoming laser beam 2. FIG. 4a also contains a plot of the backscattered light along the scanning path x. As long as the laser light is scattered back from the full medium unobstructed by an object, the backscattered light intensity has the approximately constant value $P_{bo}$. As soon as scattered components of the laser light begin to fall on the strongly absorbent object, the total scattering power is reduced, it attains a minimum value $P_{bm}$ when the backscattering occurs practically only in the vicinity of the object 4. The backscattered light intensity begins rising again when the path of the incoming beam crosses the opposite boundary of the object 4 and attains the maximal value $P_{bo}$ when the scattering is again unobstructed. Because of the bell shape of the intensity profile corresponding to FIGS. 2a and 2b, the profile of the backscattered power $P_b$ will appear broadened with respect to the actual contours of the object.

FIG. 4b shows the same scanning motion of the laser beam 2, whereby however, an object 4' is detecting having a surface extent smaller than the cross-section of the laser beam 2. From the corresponding diagram for the backscattered light power $P_b^0$, which falls to a minimal value $P_{bm}$ in the vicinity of the object 4', an indication of the extent of the object is again obtained. Here as well, the profile of the backscattered power along the scanning path is broadened with respect to the actual dimensions of the object.

From the diagrams of FIGS. 4a and 4b, conclusions about the depth at which the object lies within the medium 1 can be drawn insofar as the absorption properties of the object 4 or 4' are known.

In the case of a strongly reflecting object, the profile of the backscattered light power will rise above the normal value $P_{bo}$ to attain a maximum. Here as well, the plot of the backscattered light will be broadened over and against the actual size of the object.

In FIG. 5 an apparatus for the detection and imaging of an object 4 buried in a medium 1 is represented. A laser 11 emits a collimated beam 2, which passes through the middle aperture 12 of a duplexer mirror 13, which is inclined at a 45° angle with respect to the laser beam 2. The laser beam 2 then falls on the scanning mirror apparatus 14 comprising two mirrors 15 and 16, rotating about different axes. With the orientation of the mirrors 15 and 16 shown, the laser beam 2 is normally incident on the surface of the scattering medium 1 and penetrates the surface. By rotation of the scanning mirrors 15 and 16, the laser beam is deflected over the surface of the scattering medium in the direction of the arrow 5.

The diameter of the entry region 3 (cross-section) of the laser beam 2 at the surface of the medium should be adjusted to a minimum value, preferably at one tenth the diameter of the scattering zone S. This insures that the intensity along the axis of the beam 2 in the medium is sufficient for a good range, and simultaneously that the gapless scanning of a given area does not require too much time. To avoid image distortion, the distance of the scanning mirror arrangement 14 to the surface of the medium 1 is adjusted so that the angle of incidence of the laser beam is never greater than 10° during scanning.

The backscattered light radiation 2b is guided by the mirrors 16 and 15 and the mirroring surface of the duplexer mirror 13 to a receiver 17 and measured there.

With the aid of the two-axis scanning mirror arrangement 14, which deflects the light beam 2 and the instantaneous field of view of the receiver 17 in a raster over the surface of the medium, a rectangular section of the surface of the medium can be scanned by deflection of the mirror axes in a meander pattern or otherwise.

The mirrors 13, 15 and 16 as well as the receiving angle range of the receiver are so designed that either the entire backscattered light power which is scattered back to the acceptance range of the receiver or only a circular region (halo) around the position of the entry area 3 is detected. Simple examples of such detectors are represented in FIGS. 6a and 6b.

Receiver $17_1$ consists according to FIG. 6a of a light detector 18 onto which a ray bundle coming from the duplexer mirror 13 is focused by means of a collector lens 19. The focal length f is chosen so that at the given diameter D of the detector surface the hereby defined angle of view D/f of the receiver includes the complete scattering zone S.

In the second case, according to FIG. 6b, two collector lenses 21 and 22 are employed for the receiver $17_2$. A circular aperture 23, shown also in a top view in FIG. 6b, is placed between the lenses 21 and 22. A non-transparent insert (24) obscures the center of the scattering zone S allowing only light from its periphery (halo) to pass through the circular aperture 23 to the detector. The light passing through the aperture 23 is then concentrated by means of the second collector lens 22 onto the detector 18. The light detector 18 can in the case of either receiver display angular discrimination, as for instance a quadrant detector, so that not only the total power of the light reemitted from the scattering zone, but also its angular dependence can be evaluated. If it is thus determined that the scattering zone is not circularly symmetrical, conclusions can be drawn from the angular distribution of the light returned from the scattering zone concerning the form of or course of the boundary of an object buried in the medium. This can lead to a more sensitive method of detection and imaging of "one dimensional" objects and structures such as wires, blood vessels, etc.

Obscuring the central region of the scattering zone has the following advantages for certain fields of application.

As discussed above in connection with FIGS. 2 and 4, the percentage variation of the intensity profile of the backscattered light power $P_b$ produced by the presence of an absorbent buried object is not greatest at the center of the scattering zone where the intensity maximum occurs but in the halo region outside the entry region 3 of the laser beam. This is illustrated in FIG. 7 for the case of stationalry illumination of a medium 1 by a laser beam 2. $P_{b1}$ represents the intensity distribution of the backscattered light power $P_b$ for the case in which no object is present in the path of the laser beam through the medium. The broken bell curve $P_{b2}$ represents the intensity distribution of the backscattered light power over the region of the scattering zone in the case that a strongly absorbent object 4., also indicated with a broken line contour, lies in the path of the beam 2. The area under the curve $P_{b1}$, corresponding to the total intensity of the backscattered light power, is greater than that under the curve $P_{b2}$. The ratio of these two curves is a measure of the resolution of a device which is provided with a receiver $17_1$ according to FIG. 6a. If however, a receiver $17_2$ according to FIG. 6b is used, in which a central region B is blocked out by the central insert 24, then the ratio of the total intensity of unobstructed scattering to scattering obstructed by an object 4 can be improved. For unobstructed backscattering the total power received by detector 18 of receiver $17_2$ corresponds to the singly shaded area $F_1$ to either side of the obscured region in FIG. 7. When a buried object 4 lies in the path of the laser beam 2, the total intensity received by the pilot detector 18 of receiver $17_2$ corresponds to the doubly shaded area $F_2$ to either side of the obscured region. The ratio $F_1/F_2$ is however, much greater than the ratio of the total areas under the bell shaped curves $P_{b1}$ and $P_b$. The resolution of a device provided according to FIG. 6b with the receiver $17_2$ is correspondingly greater.

The output signals of receiver 17 are registered on a raster display device synchronously with the point scanning of the medium surface in x and y directions. After each completed scanning cycle, the image can be either stored or erased. The image point size on the raster display device, which is fixed by the electronics and determined by the sweep frequency along the scanning path or the density of the scanning cells on the imaging device, will be restricted according to the application to a range between the diameter of the scanning laser beam 2 and the mean diameter of the scattering zone S.

The apparatus described hereabove in principle can be improved by various devices shown in FIG. 5.

For suppression of background radiation impairing reception an interference filter 31 with good transmission at the emission wavelength of the laser 11 is placed in the path of the incoming light to the receiver 17.

The beam of the laser 11 can be pulsed to advantage by a chopper 32 at fixed frequency. At the receiving end, a narrow band frequency filter 33 tuned to the chopper frequency is connected to the output of the receiver 17 in order to selectively amplify light which has passed through the chopper. By this means the processing of the output signal of the receiver can be made largely independent of the background radiation and electronic noise of the photodector 18.

On scanning the medium, the evaluation can be disturbed by reflections at the surface of the medium due to the passage of the laser beam from optically sparse to optically dense media. These interfering reflections can be suppressed by linearly polarizing the laser beam 2 by means of a polarization filter 34. Contrary to the scattered light returned from the depths of the medium, which is totally depolarized by multiple scattering, the reflected light retains the polarization direction of the incident light. This reflected radiation can therefore be suppressed by a second polarization filter 35 placed in the path of the incoming light to the receiver 17 if the polarization directions of the filters 34 and 35 are perpendicular to one another.

The evaluation and display of the receiver's signals, on a raster display device 25, for example, can proceed according to a number of different processes belonging to the state of the art. If only information about the differential variations of the output signal is desired, which contain the actual image information, the output signal of the receiver can, for instance be ignored below a given threshold, processing occuring only above this level; if the laser beam is modulated (chopped), only the a.c. component need be evaluated.

With the procedure and device described, information about objects buried in a medium may be obtained from which the size and, upon suitable evaluation at least partially, their depth in the medium may also be determined.

The devices represented in FIG. 5 can be applied essentially only when the observed scattering media have well defined smooth surfaces and when the scattering centers are homogeneously distributed. If this is not the case, the device described is to be modified according to FIG. 8.

According to FIG. 8, two lasers 11' and 11" are used, each emitting collimated light beams at the wavelengths $\lambda'$ and $\lambda''$. The light rays of these two lasers are coaxially aligned by means of a dichroic mirror 41. The resultant combined beam then passes, as in the embodiment example according to FIG. 5, through the aperture 12 of a duplexer mirror 13 and is deflected by the scanning mirror arrangement 14 of the scanning mirror 15 and 16 in the direction of the surface of the medium 1. Scanning proceeds as in the device according to FIG. 5.

The backscattered light radiation 2b is deflected by the scanning mirror arrangement 14 and the duplexer mirror 13 onto a second dichroic mirror 42 and there separated into the two wavelength components. Light of wavelength $\lambda'$ from the laser 11' falls on receiver 17': light of wavelength $\lambda''$ from laser 11" falls on receiver 17". The receivers can again be constructed as indicated in FIGS. 6a and 6b. In addition the devices shown in FIG. 5 for the improvement of the resolution such as interference filters, polarization filters and frequency filters can be provided as well. The output signals of the receiver 17' and 17" are, as mentioned above, calibrated and input to an evaluation and registering device 43. In this device the difference signal of the two receivers is evaluated and registered after suitable corrections. If the wavelengths $\lambda'$ and $\lambda''$ of the two lasers are chosen, such that the scattering cross-section of the medium 1 is essentially the same for both wavelengths, then the corrected difference signal of the two receivers 17' and 17" is independent of the surface contour as well as of inhomogenities in the medium. This difference signal can then be used as well for the imaging of buried objects as described in the realization example according to FIG. 5. An extension to a multispectral imaging procedure is also possible. Applications of the procedure and the device according to the invention are as follows.

1. Imaging of inhomogenities such as density fluctuations, foreign objects, air bubbles, flaws, tears, laminations, thickness fluctuations in otherwise homogeneous materials such as porcelain ceramics, polytetrafluorethylene, PVC, glass fibers, glues, etc. A device according to FIG. 5 in which the laser operates in continuous wave mode is suitable for these purposes.

2. Examination of materials with nonplanar surfaces, modeled form or inhomogeneous composition, for inhomogenities; for this purpose light rays of several wavelengths will be used.

3. Detection of objects such as motor vehicles, landscape and tree silhouettes, objects at the bottom of the sea, etc., with a device according to FIG. 8, i.e., employing the two wavelength procedure. Pulsed lasers of high repetition frequency which simultaneously emit fundamental and harmonic wavelengths, such as the Neodymium; YAG laser, are preferable. In general, high power cw lasers with several wavelength components are applicable.

4. Medical investigations such as the detection of foreign bodies, tissue anomalies, and the paths of blood vessels in biological tissue, may be made. Such investigations can be performed with a one wavelength procedure according to FIG. 5. Likewise a two- or more wavelength process is possible if the object to be investigated displays specific absorption or reflection properties dependent on the wavelengths utilized. In this manner a multispectral procedure can obtain information, for example, on the oxygen saturation of hemoglobin in living tissue in spite of scattering by other absorbing tissue components. For such an application, tunable dye lasers or multiple wavelength argon and krypton lasers may be used.

In all cases conventional mirror galvanometer scanners can be used. Silicon PIN diodes and Si-avalanche diodes are suitable for the detector.

Although the invention has been described with reference to specific example embodiments, it will be appreciated, that it is intended to cover all modifications and equivalents within the scope of the appended claims.

What is claimed is:

1. A method for detecting and imaging objects surrounded by a scattering medium comprising: illuminating the scattering medium with a collimated light beam incident upon and penetrating said medium; scanning the collimated light beam through a region of the scattering medium and at successive positions along a scanning path across a selected scanning area; detecting the back scattered light in the scattering zone around the locus of incidence of the collimated light beam on the scattering medium and measuring the intensity of the back scattered light from the scattering zone at successive positions along the scanning path across said scanning area; registering the measured intensity of light from the scattering zone at said successive positions along the scanning path; and associating differential measurements registered along the scanning path with the possible presence of an object.

2. The method of claim 1, further comprising the step of blocking or obscuring the back scattered light from the center of the scattering zone, thereby detecting and measuring only the back scattered light from the periphery of the scattering zone and thereby increasing the sensitivity to intensify differences between successive positions of the scanning path.

3. The method of claim 1, wherein the step of illuminating the scattering medium with a collimated light beam comprises illuminating the medium by light of at least two constituent wavelengths, and further comprising the steps of: separating the backscattered light from said scattering zone into at least two light paths of said at least two constituent wavelengths; detecting and measuring the intensity of the light at said at least two constituent wavelengths; measuring the difference in intensity between said at least two constituent wavelengths at successive positions across the scanning paths; registering said difference measurements for successive positions along the scanning path; and associating differences in said difference measurements with the presence of possible objects in the scattering medium.

4. An apparatus for detecting and imaging objects in a scattering medium by light irradiation, comprising: light source means delivering a collimated light beam incident upon and penetrating said scattering medium in a scattering zone; optical scanning means operatively arranged relative to said light source means and said scattering medium for deflecting the light beam through a region of the scattering medium at successive positions along a scanning path across a specified scanning area; photodetector means operatively arranged for receiving and detecting substantially the full angular distribution of backscattered light returning from said scattering zone around the locus of incidence of the light beam, said photodetector means further comprising means for measuring the intensity of said backscatter light received from the scattering zone; and register means for registering the values of said intensity measurements at said successive positions along the scanning path, said apparatus further comprising first polarization filter means placed in the path of said collimated light beam incident on the scattering medium for linear polarization of said incident light beam, and second polarization filter means having a polarization direction perpendicular to the first polarization filter means, said second polarization filter means being interposed in the path of the backscattered light received from the scattering zone.

5. The apparatus of claim 4, wherein said optical scanning means comprises scanning mirror means constructed and arranged for deflection of the collimated light beam along the scanning path across said selected scanning area, said scanning mirror means being arranged for deflection of the backscattered light from said scattering zone to said photodetector means.

6. The apparatus of claim 4, wherein said photodetector means further comprise aperture means comprising a central insert, said aperture means being positioned in the light path of backscattered light from said scattering zone to obscure the central portion of said scattering zone and block the backscattered light from the center of said scattering zone.

7. The apparatus of claim 4, wherein said light source means is selected to deliver a collimated light beam characterized by light of a selected wavelength, and further comprising interference filter means interposed in the path of the backscattered light from said scattering zone, said interference filter means having a characteristic wavelength corresponding substantially to the wavelength of light of the incident collimated light beam thereby to suppress background radiation.

8. The apparatus of claim 4, further comprising light chopper means interposed in the path of the incident collimated light beam delivered by said light source means for modulating the incident light beam at a characteristic frequency, and frequency filter means tuned to said modulating frequency for selectively passing signals corresponding to light which has passed through said light chopper means, said frequency filter means being coupled to the output of said detector means.

9. The apparatus of claim 4, wherein said light source means comprises first and second light sources for delivering a collimated light beam composed of light of at least two different constituent wavelengths; optical separator means interposed in the path of backscattered light from the scattering zone for separating the backscattered light beam into said at least two constituent wavelengths; wherein said detector means comprises first and second detectors operatively arranged for respectively receiving the separated light of said at least two constituent wavelengths; wherein said means for measuring the intensity of backscattered light comprises first and second measuring means for measuring the intensity of light at said at least two constituent wavelengths; and further comprising means for measuring the difference between the intensity measurements of the light of said at least two constituent wavelengths at successive positions along the scanning path; and wherein said register means is operatively arranged for registering said difference measurements at successive positions along the scanning path.

10. The apparatus of claim 9, wherein said first and second light source means are selected and operatively arranged to deliver the light of said at least two constituent wavelengths, at wavelengths selected with reference to the scattering medium containing the objects to be detected and imaged so that the scattering medium has approximately the same absorption properties at both said at least two constituent wavelengths.

11. The apparatus of claim 9, wherein said first and second light sources comprise lasers.

12. The apparatus of claim 9, wherein said optical separator means comprises a dichroitic mirror.

13. The apparatus of claim 4, wherein said register means comprises a raster image display means for plotting and displaying the intensity measurements for visual indication of the possible presence of objects in the scattering medium.

14. The apparatus of claim 4, wherein said light source means comprises at least one laser.

15. The apparatus of claim 4, wherein said detector means comprises a quandrant detector means for angular discrimination in the detection of backscattered light from the scattering zone.

* * * * *